US00PP19318P2

(12) United States Plant Patent
Hooijman

(10) Patent No.: US PP19,318 P2
(45) Date of Patent: Oct. 14, 2008

(54) *GYPSOPHILA* PLANT NAMED 'ESM CHISPA'

(50) Latin Name: *Gypsophila hybrida*
Varietal Denomination: Esm Chispa

(75) Inventor: Aloysius A. J. Hooijman, Aalsmeer (NL)

(73) Assignee: ESmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/903,796

(22) Filed: Sep. 25, 2007

(51) Int. Cl.
*A01H 5/00* (2006.01)

(52) U.S. Cl. ..... Plt./354

(58) Field of Classification Search ..... Plt./354
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Gypsophila* plant named 'Esm Chispa', characterized by its compact and mounding growth habit; uniform and freely flowering habit; small semi-double white-colored flowers; and good postproduction longevity and garden performance.

2 Drawing Sheets

Botanical designation: *Gypsophila hybrida.*
Cultivar denomination: 'Esm Chispa'.

BACKGROUND OF THE INVENTION

The present invention relates to a new and distinct cultivar of *Gypsophila* plant, botanically known as *Gypsophila hybrida,* grown commercially as a cut flower, and hereinafter referred to by the name 'Esm Chispa'.

The new *Gypsophila* is a product of a planned breeding program conducted by the Inventor in El Quinche, Pichincha, Ecuador. The objective of the breeding program is to create new freely flowering pot-type *Gypsophila* cultivars.

The new *Gypsophila* originated from an open-pollination made by the Inventor in El Quinche, Pichincha, Ecuador in August, 2001 of a proprietary selection of *Gypsophila hybrida* identified as Line 34, not patented, as the female, or seed, parent with an unknown selection of *Gypsophila hybrida.* The cultivar Esm Chispa was discovered and selected by the Inventor as a flowering plant from within the progeny of the stated open-pollination in a controlled environment in El Quinche, Pichincha, Ecuador.

Asexual reproduction of the new *Gypsophila* by cuttings in a controlled environment in El Quinche, Pichincha, Ecuador since October, 2002, has shown that the unique features of this new *Gypsophila* are stable and reproduced true to type in successive generations.

SUMMARY OF THE INVENTION

The cultivar Esm Chispa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Chispa'. These characteristics in combination distinguish 'Esm Chispa' as a new and distinct cultivar of *Gypsophila:*

1. Compact and mounding growth habit.
2. Uniform and freely flowering habit.
3. Small semi-double white-colored flowers.
4. Good postproduction longevity and garden performance.

In side-by-side comparisons conducted in El Quinche, Pichincha, Ecuador, plants of the new *Gypsophila* differed from plants of the female parent selection in the following characteristics:

1. Plants of the new *Gypsophila* were more compact than plants of the female parent selection.
2. Plants of the new *Gypsophila* had smaller flowers than plants of the female parent selection.
3. Plants of the new *Gypsophila* were more freely flowering than plants of the female parent selection.

Plants of the new *Gypsophila* can be compared to plants of the *Gypsophila* cultivar Dangypflash, disclosed in U.S. Plant Pat. No. 12,422. In side-by-side comparisons conducted in El Quinche, Pichincha, Ecuador, plants of the new *Gypsophila* differed from plants of the cultivar Dangypflash in the following characteristics:

1. Plants of the new *Gypsophila* were more compact than plants of the cultivar Dangypflash.
2. Plants of the new *Gypsophila* had shorter internodes than plants of the cultivar Dangypflash.
3. Plants of the new *Gypsophila* had shorter leaves than plants of the cultivar Dangypflash.
4. Plants of the new *Gypsophila* were more freely flowering than plants of the cultivar Dangypflash.
5. Flowers of plants of the new *Gypsophila* were longer-lasting than plants of the cultivar Dangypflash.

BRIEF DESCRIPTION OF THE PHOTOGRAPHS

The accompanying photographs illustrate the overall appearance of the new *Gypsophila.* These photographs show the colors as true as it is reasonably possible to obtain in colored reproductions of this type. Colors in the photographs may differ slightly from the color values cited in the detailed botanical description which accurately describe the colors of the new *Gypsophila*.

The photograph on the first sheet comprises a side perspective view of a typical flowering plant of 'Esm Chispa' grown in a container.

The photograph on the second sheet is a close-up view of typical flowers of 'Esm Chispa'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in El Quinche, Pichincha, Ecuador during the winter in containers in an outdoor nursery and under conditions and practices which approximate those generally used in commercial cut *Gypsophila* production. During the production of the plants, day temperatures ranged from 11° C. to 28° C. and night temperatures ranged from 5° C. to 11° C. Plants were pinched one time about five weeks after planting and were grown under long day/short day conditions. Measurements and numerical values represent averages for typical 15-week old flowering plants.

Botanical classification: *Gypsophila hybrida* cultivar Esm Chispa.

Commercial classification: Pot-type *Gypsophila*.

Parentage:

*Female, or seed, parent.*—Proprietary selection of *Gypsophila hybrida* identified as Line 34, not patented.

*Male, or pollen, parent.*—Unknown selection of *Gypsophila hybrida,* not patented.

Propagation:

*Type.*—By cuttings.

*Time to initiate roots.*—About 16 to 21 days at 17° C. to 25° C.

*Time to produce a rooted cutting.*—About five to six weeks at 17° C. to 25° C.

*Root description.*—Fleshy, medium in thickness to thick; 162C in color.

*Rooting habit.*—Freely branching.

Plant description:

*Appearance.*—Perennial; compact and mounding growth habit; inverted triangle form. Freely flowering; small white-colored flowers arranged in symmetrical and moderately dense compound cymes. Vigorous growth habit.

*Branching habit.*—After pinching, about eight lateral branches develop.

*Plant height.*—About 45 cm.

*Plant diameter or spread.*—About 55 cm.

*Lateral branches.*—Length: About 41 cm. Diameter: About 4.6 mm. Internode length: About 3.7 cm. Strength: Strong. Texture: Glabrescent. Color: 138A.

Foliage description:

*Arrangement.*—Opposite, decussate, simple; sessile.

*Length.*—About 5.3 cm.

*Width.*—About 1.5 cm.

*Shape.*—Narrowly lanceolate.

*Apex.*—Acute.

*Base.*—Cuneate.

*Margin.*—Entire.

*Texture, upper and lower surfaces.*—Smooth, glabrous; waxy.

*Venation pattern.*—Parallel.

*Color.*—Developing foliage, upper surface: 147A. Developing foliage, lower surface: 139A. Fully expanded foliage, upper surface: 139A; venation, 139A. Fully expanded foliage, lower surface: 137A; venation, 146C.

Flower description:

*Flower arrangement and habit.*—Symmetrical compound cymes with numerous small white-colored flowers, flowers rotate. Very freely flowering, about 5,200 flowers per inflorescence. Flowers face mostly upright.

*Flowering response.*—In Ecuador, plants flower year round. Plants begin flowering about 12 weeks after planting.

*Post-production longevity.*—On the plant, flowers last for about three weeks. Flowers persistent.

*Fragrance.*—Slightly fragrant; pleasant.

*Inflorescence height.*—About 41 cm.

*Inflorescence diameter.*—About 48 cm.

*Flower diameter.*—About 6 mm.

*Flower depth (height).*—About 5 mm.

*Flower buds.*—Length: About 2 mm. Diameter: About 1.7 mm. Shape: Nearly globose. Color: N199A.

*Petals/petaloids.*—Quantity per flower: About 25 arranged in clusters. Length: About 3.5 mm. Width: About 1.5 mm. Shape: Oval to spatulate. Apex: Truncate, emarginate or obtuse. Margin: Entire. Texture, upper and lower surfaces: Smooth, glabrous; waxy. Color: When opening and fully opening, upper surface: Close to N155D; towards the base, close to 144A; color becoming closer to 161B with development. When opening and fully opening, lower surface: Close to N155D.

*Sepals.*—Quantity per flower: About five to seven fused to form a cup-shaped calyx. Length: About 2.8 mm. Width: About 1.2 mm. Shape: Roughly linear. Apex: Acute. Margin: Entire. Texture, upper and lower surfaces: Smooth, glabrous. Color: When developing, upper surface: 148A. When developing, lower surface: N199A. Fully developed, upper and lower surfaces: 146A.

*Peduncles.*—Length: About 2.5 cm. Diameter: About 6 mm. Strength: Strong. Angle: About 49° from vertical. Texture: Smooth, glabrous. Color: 138A.

*Pedicels.*—Length: About 4.2 mm. Diameter: About 0.25 mm. Strength: Strong. Angle: About 38° from vertical. Texture: Smooth, glabrous. Color: 147A.

*Reproductive organs.*—Stamens: Quantity per flower: Six. Anther shape: Reniform to globose. Anther length: Less than 1 mm. Anther color: 155B. Pollen amount: Scarce. Pollen color: Close to 155B. Pistils: Quantity per flower: One. Pistil length: About 5.3 mm. Style length: About 2.8 mm. Style color: Close to 155D. Stigma shape: Curved apiculate. Stigma color: Close to 155D. Ovary color: 143C; occasionally towards the apex, 165A. Seed/fruit: Seed and fruit production has not been observed.

Disease/pest resistance: Plants of the new *Gypsophila* have not been shown to be resistant to pathogens and pests common to *Gypsophila*.

Garden performance: Plants of the new *Gypsophila* have been observed to tolerate wind, rain and temperatures ranging from about 7° C. to about 30° C.

It is claimed:

1. A new and distinct *Gypsophila* plant named 'Esm Chispa' as illustrated and described.

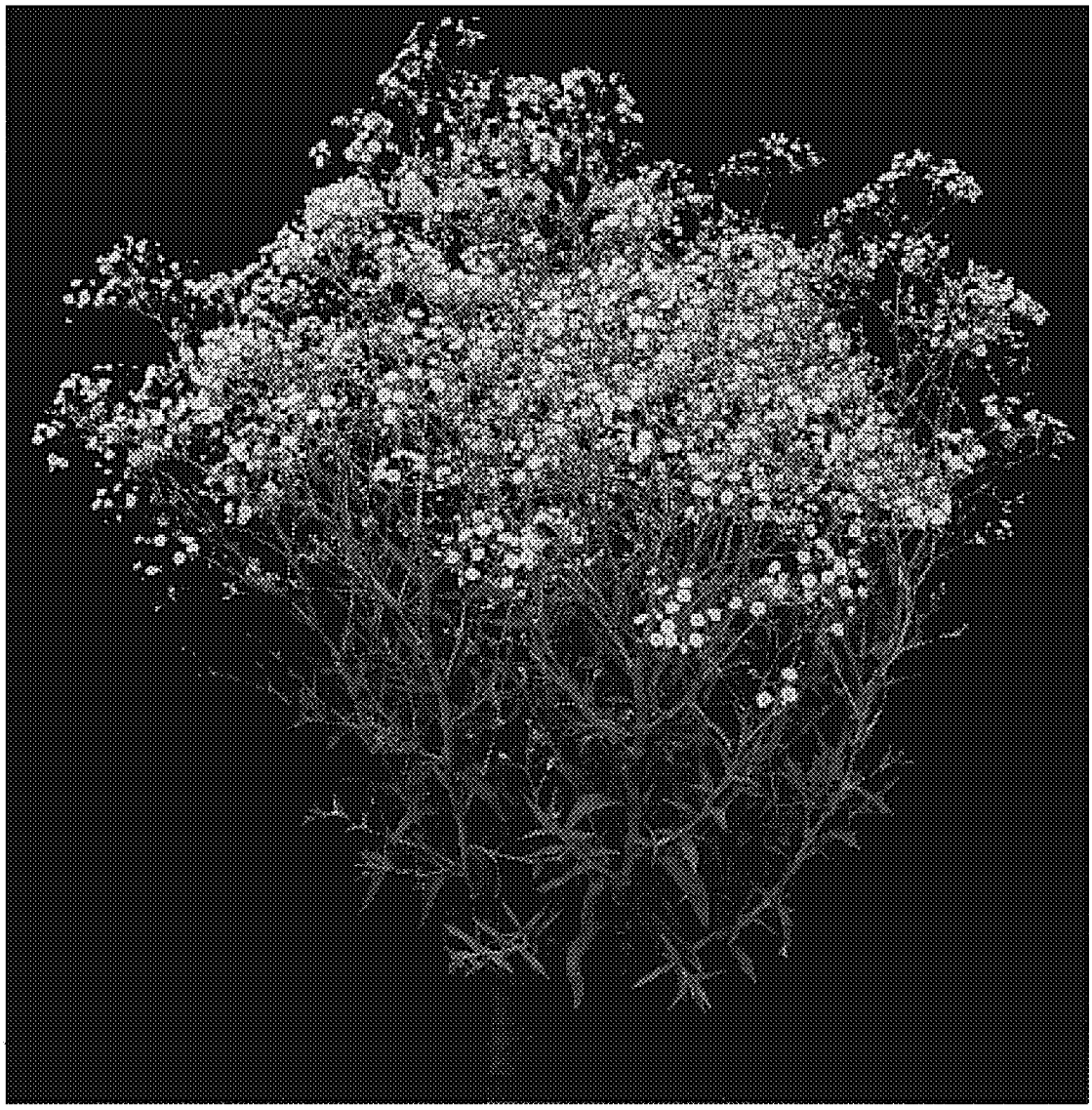

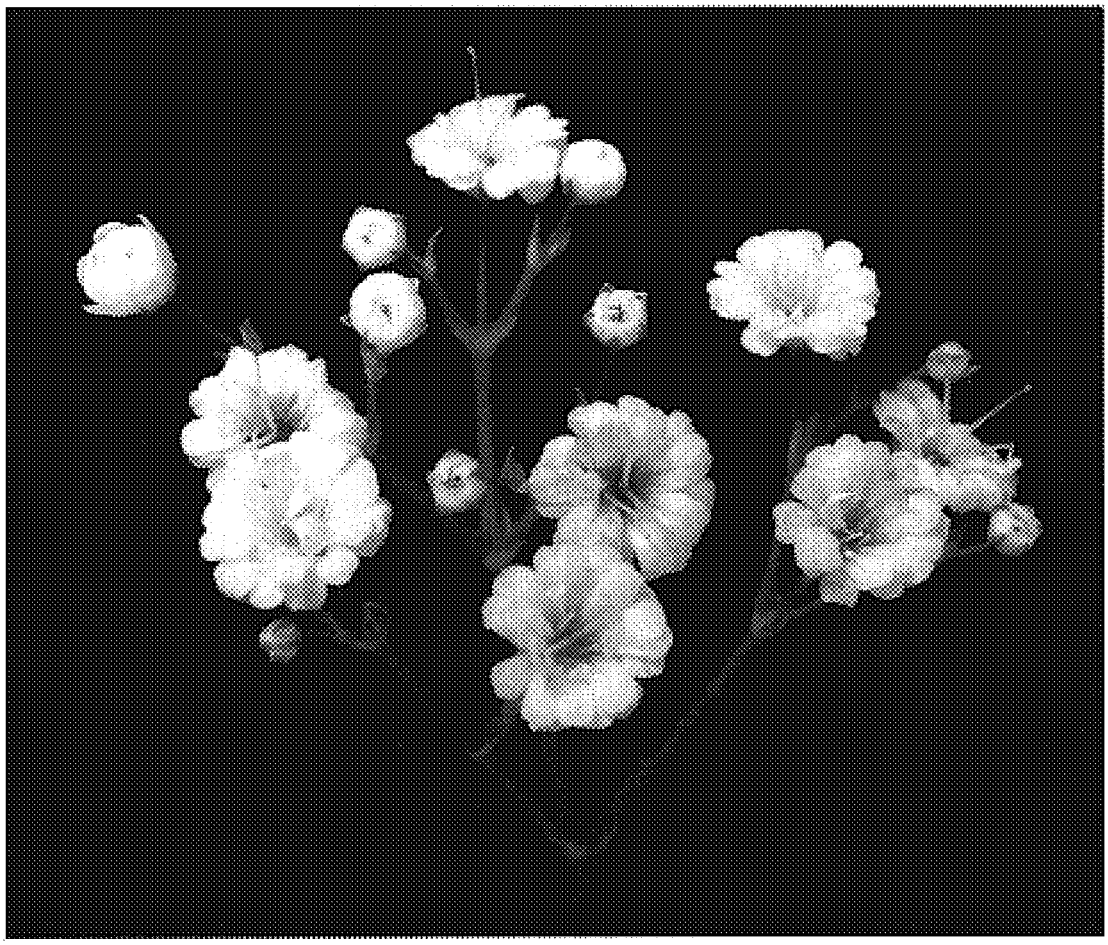

* * * * *